US005322059A

United States Patent [19]

Walther

[11] Patent Number: 5,322,059

[45] Date of Patent: Jun. 21, 1994

[54] BREATHING MASK WITH FLOW INDICATOR FOR THE RESPIRATION AIR

[75] Inventor: Hans-Joachim Walther, Lübeck, Fed. Rep. of Germany

[73] Assignee: Dragerwerk AG, Lubeck, Fed. Rep. of Germany

[21] Appl. No.: 998,415

[22] Filed: Dec. 29, 1992

[30] Foreign Application Priority Data

Jan. 24, 1992 [DE] Fed. Rep. of Germany ....... 4201832

[51] Int. Cl.[5] .......................... A62B 7/00; A62B 9/00; G08B 3/00; A61M 16/00

[52] U.S. Cl. .......................... 128/205.23; 128/205.25; 128/202.22

[58] Field of Search ...................... 128/205.23, 205.25, 128/200.23, 202.22, 200.24, 206.21, 206.28

[56] References Cited

U.S. PATENT DOCUMENTS 440,713 11/1890 Krohne et al. ................ 128/205.23
4,098,271 7/1978 Maddock ...................... 128/202.22
4,832,015 5/1989 Nowacki et al. .............. 128/205.23
4,905,683 3/1990 Cronjaeger ..................... 128/202.22
5,035,239 7/1991 Edwards ........................ 128/205.23

*Primary Examiner*—Edgar S. Burr
*Assistant Examiner*—Kimberly L. Asher
*Attorney, Agent, or Firm*—McGlew and Tuttle

[57] ABSTRACT

A breathing mask with a fan for feeding respiration air into the interior space of the mask has a flow indicator for indicating a necessary respiration air flow at the air outlet end of the fan connection. In order for this indicator to be directly recognizable by the mask user in his field of vision, the opening of the air outlet end (4) shall be closed at least partially by a flow plate, which is movably mounted on a guide structure (11, 20) such that it emerges into the field of vision of the mask user in the presence of air flow, and guides the respiration air flow along the inner side of the window (10). If the respiration air flow is insufficient, the flap jumps back, and warning windows appear, instead, in the range of vision of the mask user.

8 Claims, 1 Drawing Sheet

FIG. 1
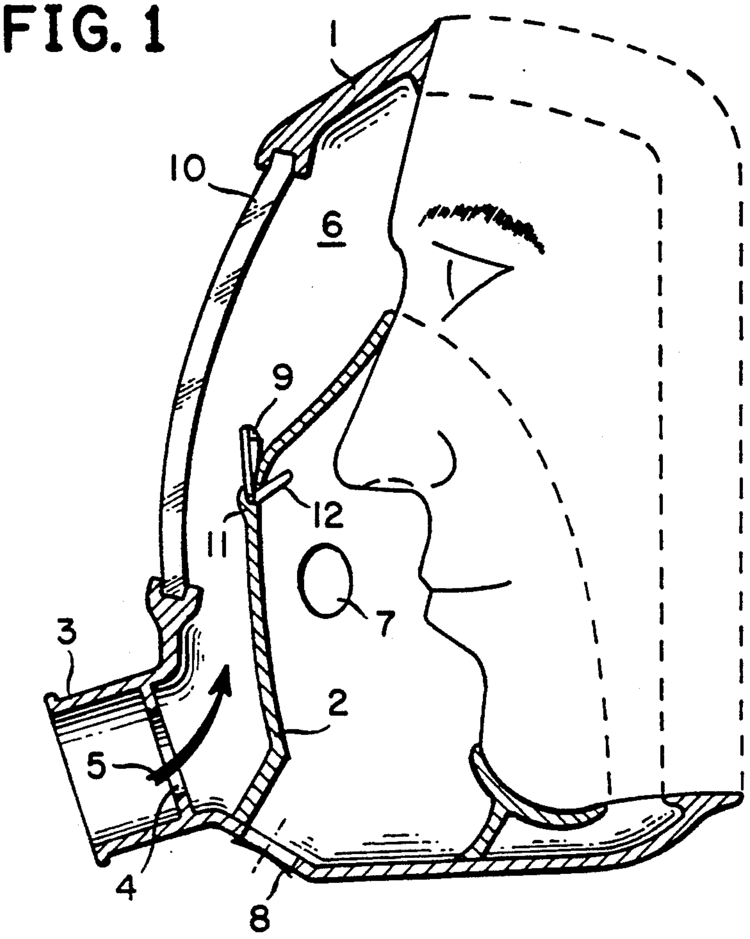
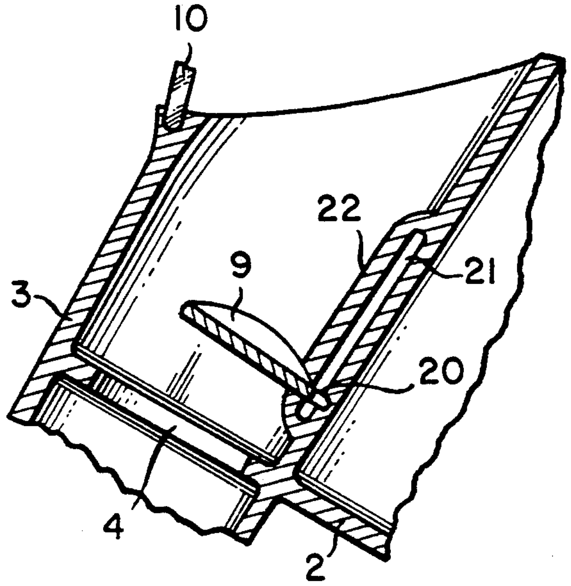
FIG. 2

BREATHING MASK WITH FLOW INDICATOR FOR THE RESPIRATION AIR

FIELD OF THE INVENTION

The present invention pertains to a breathing mask with a fan, which feeds the respiration air into the interior space of the mask via a respiration connection, is connected to the mask body through a fan connection, and at the air outlet end of which a flow indicator indicating the fan air flow is arranged.

BACKGROUND OF THE INVENTION

Such a breathing mask was described in West German Offenlegungsschrift No. DE-OS 30,32,371. A protective mask with a protective helmet located on it is provided there with a fan air inlet means, which ends at the eye level of the mask user, and is provided with a flow indicator there. The air flow is maintained by the fan, and it deflects a vane located at the air outlet end more or less to varying degrees, depending on the output of the fan. The fan air flowing into the interior space of the mask from the rear side of the mask user escapes from the interior space of the mask in the downward direction along an open protective visor that can be folded up. To facilitate reading of the deflected vane, a mirror surface, via which the mask user is able to observe the vane, is arranged on the visor, on its inner side, at the eye level in the visual range.

It is disadvantageous in the known state of the art that the necessary fan output can be monitored only insufficiently or with additional reading aids. A mirror arrangement for reading the position of the vane involves, among others, the risk that due to the mirror-inverted reading, the mask user might erroneously consider an insufficient delivery output to be still sufficient.

SUMMARY AND OBJECTS OF THE INVENTION

The primary object of the present invention is to improve a breathing mask of the above-described type such that sufficient supply of respiration air will be directly recognizable in the visual range of the mask user.

This task is accomplished in that in a full face-piece mask, the air outlet end opens into the interior space of the mask in the nose and mouth area, and that the opening of the air outlet end is closed at least partially by a flow plate, which is movably mounted on a guide means such that when the necessary flow pressure generated by the fan is present, the plate guides, against a restoring force, the respiration air flowing from the air outlet end along the window, and thus it extends into the field of vision of the mask user to the extent that it will be recognizable by him.

The advantage of the present invention is essentially the fact that in the case of sufficient air supply by the fan, the mask user is able to immediately recognize, due to the flow plate entering the field of vision, whether the air flow is sufficient, on the one hand, and that, on the other hand, the air is guided by the fan along the window, protecting it from fogging due to the moisture present in the air. The emergence of the flow plate into the window can also be observed from the outside, so that the sufficient fan output can also be checked at the time of testing or checking the complete device during maintenance or repair.

In a simple embodiment, the flow plate can be attached to a hinge as a guide means, on which a restoring force is generated by, e.g., a spring acting on the said hinge, wherein the said restoring force is strong enough to press the plate against the air outlet end, so that the plate will disappear from the field of vision of the mask user, and the flow plate will again emerge into the field of vision of the mask user against the restoring force only in the case of sufficient flow output.

The flow plate is advantageously provided with a vane, which is connected in one piece with the flow plate, but it is bent by a certain angle in relation to this and in relation to the hinge axis. This angle corresponds to the angle through which the flow plate rotates in its two intended states of indication (sufficient fan output, insufficient fan output). Consequently, if there is a sufficient fan output, the flow plate will appear in the field of vision of the mask user, and the warning vane will disappear. However, if the flow output of the fan is insufficient, the flow plate will disappear from the field of vision, and the warning vane will appear, instead, in the field of vision of the mask user. The flow plate and the warning vane may carry different color markings. For example, the flow plate is green and the warning vane is red, so that an immediately visible indication of correct or incorrect function can be given.

In another advantageous embodiment, the guiding means is designed as a shifting guide, along which the flow plate can be shifted in the direction of flow. The restoring force is brought about by a restoring spring acting on the shifting guide. The restoring force may also be generated by the own weight of the flow plate.

Another possibility of arranging the flow plate is to connect it in one piece to the air outlet end, so that it will cover the opening of the air outlet end like a tongue. In this case, the flow plate is moved from its resting position into the visual range of the mask user only in the case of sufficient air flow, and the elastic connection between the flow plate and the air outlet end will provide for the elastic restoring forces of the material for the necessary counteracting force. The flow plate can be arranged at the air outlet end in the form of a film hinge made of plastic.

If a full face-piece mask is used with an inner half mask, it is advantageous to provide the air outlet end at the point of connection between the mask body and the inner half mask. This is a favorable site for the flow plate in terms of the deflection of the respiration air flow against the inner side of the eye-protective lens, on the one hand, and, on the other hand, it is a favorable location for feeding the respiration air to the mask user via the inhalation valves of the inner half mask.

In a full face-piece mask with inner half mask, it is favorable to design the flow plate as an inhalation valve plate, which opens during the inhalation phase and closes during the expiration phase, thus ensuring a directed respiration air flow from the fan in the direction of the inner half mask. The inhalation valves in the inner half mask, which are otherwise necessary, can now be omitted.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic the sectional view of a breathing mask with inner half mask; and FIG. 2 is a schematic sectional view of an embodiment of the flow plate.

DETAILED DESCRIPTION OF THE PREFERRED EMBODIMENT

FIG. 1 shows a breathing mask 1 with an inner half mask 2, which is supplied with respiration air from a fan, not shown, via a fan connection 3. At the air outlet end 4 of the fan connection 3, the respiration air flows along the flow arrow 5 into the interior space 6 of the mask. From there, the respiration air flows through the inhalation valve 7 and into the inner half mask 2 during the inhalation phase of the mask user. An expiration valve 8 opens during the expiration phase and permits expiration air to escape into the atmosphere. A flow plate 9, which is held by the air flow in the open position and is pressed around its hinge 11 into the visual range of the window 10, is located at the air outlet end 4. A warning vane 12 is arranged in a bent position on the flow plate 9, and it is also rotatable around the hinge 11. In the position of the flow plate 9 shown, the warning vane 12 disappears from the visual range of the mask user laterally beside the inner half mask 2. In the case of interruption of the flow from the fan connection 3, the flow plate 9 drops toward the air outlet end 4 because of its own gravity, and the warning vane 12 is tilted by an equal angle in the forward direction into the visual range of the window 10. The warning vane 12 is now recognizable by the mask user, indicating the malfunction of the fan to the user.

FIG. 2 shows a detail of another embodiment for the arrangement of the flow plate 9, which is held by means of a pin connection 20 along a recess 21 of a connecting link guide 22. In the case shown, the flow plate 9 is lowered, by its own weight, into the lower position from the visual range of the window 10 in the direction of the air outlet end 4 in the case of interruption of the flow from the fan connection 3. As soon as respiration air begins to flow, the flow plate 9 is raised by the flow resistance along the connecting link guide 22 into range of vision of the window 10. The length of the connecting link guide 22 may be adapted to the conditions, so that sufficient raising of the flow plate 9 into the field of vision of the mask user is guaranteed.

In the case of sufficient fan output, the flow plate 9 is shifted along the connecting link guide 22 into the upper end position. The end of the plate 9 facing the window 10 now increasingly withdraws from the window 10, as a result of which the flow cross section for the incoming air is increased.

While specific embodiments of the invention have been shown and described in detail to illustrate the application of the principles of the invention, it will be understood that the invention may be embodied otherwise without departing from such principles.

What is claimed is:

1. A breathing mask with a fan feeding respiration air into an interior space of the mask via a respiration connection, the breathing mask comprising:

a full face-piece mask including a window corresponding to a field of vision of the mask user and structure defining an interior space in a nose and ear area;

a fan connection for connecting air driven by the fan to said interior space, said fan connection having an air outlet end with an opening into said interior space;

flow indicator means for indicating fan air flow into said interior space and including a flow plate at least partially closing said opening of said outlet end and guide means for guiding movement of said flow plate between a position visible to the mask user and a position not visible to the mask user, said flow plate being movably mounted on said guide means, said flow plate being acted on by respiration fan air flowing out of said air outlet end along said window, against a restoring force, when necessary flow pressure is generated by said fan, said flow plate extending into said field of vision of the mask user for recognizing said necessary flow pressure.

2. A breathing mask according to claim 1, wherein:

said guide means includes a hinge; and when flow pressure is insufficient, said flow plate being pressed by said restoring force onto said air outlet end to disappear from said field of vision of the mask user.

3. A breathing mask according to claim 2, wherein:

a warning vane is connected in one piece to said flow plate and is introduced into said field of vision as said flow plate is pressed against said air outlet end, indicating that necessary flow pressure is not generated by said fan.

4. A breathing mask according to claim 1, wherein:

said guide means is formed as a shifting guide for guiding said flow plate essentially parallel to the respiration air flow escaping from said air outlet end.

5. A breathing mask according to claim 1, wherein:

said flow plate is elastically attached to a part of an edge area of said air outlet end.

6. A breathing mask according to claim 1, wherein:

said air outlet end opens into said interior space at a connection point between said outer mask and said inner half mask.

7. A breathing mask according to claim 6, wherein:

said flow plate is formed as an inhalation valve plate pressed, during expiration, against said air outlet end, said air outlet end forming a valve seat and said valve plate sealing said outlet end.

8. A breathing mask, comprising:

a full face piece mask including an inner half mask portion and an outer mask portion with a window, said inner half mask portion and said outer mask portion cooperating to define an interior space, said window defining a field of vision of a mask user;

a fan connection connecting a respiration connection fed with respiration air by a fan, said fan connection having an air outlet end opening into said interior space at a connection point between said outer mask and said inner mask;

a flow plate in said interior space at least partially obstructing the opening of said air outlet end, indicating fan air flow;

guide means supporting said flow plate for movement of said flow plate between a position in said field of vision of the mask user and a position out of said field of vision of the mask user, said flow plate being acted on by the respiration air flowing from said air outlet and along said window from said fan; wherein a lack of sufficient air flow generated by said fan causes said flow plate to be guided to said position out of said field of vision of the mask user, and sufficient air flow generated by said fan causes said flow plate to be guided by said guide means to said position in said field of vision of the mask user.

* * * * *